(12) United States Patent
Koizumi

(10) Patent No.: US 7,943,127 B2
(45) Date of Patent: May 17, 2011

(54) DEFENSE AND COUNTER-DEFENSE COMPOSITIONS AND METHODS

(76) Inventor: David Koizumi, Villa Park, CA (US)

( * ) Notice: Subject to any disclaimer, the term of this patent is extended or adjusted under 35 U.S.C. 154(b) by 133 days.

(21) Appl. No.: 11/958,973

(22) Filed: Dec. 18, 2007

(65) Prior Publication Data

US 2008/0095759 A1  Apr. 24, 2008

Related U.S. Application Data

(62) Division of application No. 11/101,057, filed on Apr. 6, 2005, now abandoned.

(60) Provisional application No. 60/560,772, filed on Apr. 7, 2004.

(51) Int. Cl.
*A61K 38/46* (2006.01)
*A61K 38/47* (2006.01)

(52) U.S. Cl. .................. 424/94.65; 424/94.61; 424/94.6

(58) Field of Classification Search ........................ None
See application file for complete search history.

(56) References Cited

U.S. PATENT DOCUMENTS 4,842,873 A * 6/1989 Takenawa et al. .............. 426/49
5,395,541 A 3/1995 Carpenter et al.

OTHER PUBLICATIONS

Mueen Aslam et al. "Proteases in Milk" Ilini DairyNet University of Illinois Extension Aug. 5, 1998 2 pgs.*
Leslie Ann Jones et al "Household Treatment for "Chile Burns" of the Hands" Clinical Toxicology, 25(6), 483-491 (1987).*
The great hot sauce book Jennifer Trainer Thompson "The Great Hot Sauce Book" Published by Ten Speed Press, 1995 ISBN 0898157838, 9780898157833 2 pgs.*
H.R. Maurer, "Bromelain: biochemestry, pharmacology and medical use" CMLS, Cell. Mol. Life Sci, 58 (2001) 1234-1245.

* cited by examiner

*Primary Examiner* — Irene Marx
*Assistant Examiner* — Thane Underdahl
(74) *Attorney, Agent, or Firm* — Fish & Associates, PC

(57) ABSTRACT

Contemplated compositions and methods are directed to the use of a proteinase to reduce capsaicin-induced pain sensation in a mammal. Preferably, the proteinase comprises a bromelain preparation in a liquid formulation for topical or enteral administration. In additional aspects of the inventive subject matter, a proteinase inhibitor is present in pepper spray to avoid inactivation of capsaicin by a proteinase.

7 Claims, No Drawings

DEFENSE AND COUNTER-DEFENSE COMPOSITIONS AND METHODS

This application is a divisional application of U.S. patent application Ser. No. 11/101,057 filed Apr. 6, 2005 which claims priority to provisional patent application with the Ser. No. 60/560,772, filed Apr. 7, 2004, both of which are incorporated herein by reference in their entirety.

FIELD OF THE INVENTION

Compositions and methods for personal protection, defense, and counter-defense.

BACKGROUND OF THE INVENTION

Capsaicin (Chemical name: (E)-N-((4-Hydroxy-3-methoxyphenyl)-methyl)-8-methyl-6-nonenamide) is the compound in the fruit of various peppers that is responsible for the hot taste sensation. Capsaicin is a highly potent flavoring agent and can be tasted in a dilution of greater than one in seventeen million. Despite the potency and wide range of physiological reactions in human (e.g., inflammatory agent, mucous membrane stimulant, etc.), the lethal toxic doses of capsaicin, measured in milligrams per kilogram of animal weight ranges from about 0.56 mg/kg when administered intravenously, about 190 mg/kg when consumed, to about 512 mg/kg when applied topically. Capsaicin is also the active ingredient in pepper spray, and different pepper sprays use different concentrations and solvents for delivery. Regardless of the formulation of pepper spray, pepper spray generally acts by triggering an inflammatory response (e.g., mucosal, conjunctival, and respiratory response) to thereby temporarily incapacitate a person without infliction of permanent physical harm.

Remarkably, there is no reported quick and effective neutralizing agent for capsaicin, and only relatively few treatments are known in the art to blunt perceived pain to at least some degree. For example, application of milk, baking soda paste, or honey are though to be somewhat effective to reduce the stinging sensation from the fingers and face, but residual and clearly noticeable amounts of capsaicin will generally remain on the fingers even after dozens of hand washings. Alternatively, the body surface that had contact with capsaicin can be washed with ethanol. However, ethanol application in significant quantities has typically only limited effect and is not recommended for conjunctival or internal tissue. Thus, there is a still a need for improved compositions and methods to quickly and effectively alleviate symptoms associated with inadvertent and/or undesired exposure to capsaicin.

SUMMARY OF THE INVENTION

The inventors surprisingly discovered that proteinases can be employed in compositions and methods to provide pain relief where the pain or discomfort is due to exposure to capsaicin and/or capsaicin-related compounds.

In one aspect of the inventive subject matter, a composition comprises a proteinase in a formulation for oral or topical administration, wherein the proteinase is present at a concentration effective to reduce subjective pain caused by exposure to capsaicin. Viewed from another perspective, the inventors also contemplate a kit comprising a proteinase in a formulation for oral or topical administration, wherein the kit further includes an information that is associated with the formulation to administer the formulation to a person exposed to capsaicin.

With respect to the proteinase, it is generally preferred that the proteinase is present in the composition as part of a preparation isolated from an edible plant, or more typically that the proteinase is isolated from an edible plant. Therefore, especially suitable proteinases include bromelain. Furthermore, it is generally preferred that the proteinase containing composition is in a liquid formulation, which may be sprayed to the area affected with the capsaicin, and/or may be gargled and/or ingested. Most typically, the proteinase is present in contemplated formulations at a concentration of at least 10 GDU/ml. Where desirable, an information may be associated with the packaging and/or container that includes the formulation, wherein the information may instruct a person to orally administer or to spray the formulation.

Therefore, the inventors also contemplate a method of providing relief of pain caused by exposure to capsaicin in which in one step a proteinase is provided in a formulation for oral or topical administration. In another step, an information is provided to administer the formulation in an amount effective to reduce the pain. With respect to the proteinase, the formulation, and other elements of contemplated methods, the same considerations as provided above apply.

DETAILED DESCRIPTION

The inventors surprisingly discovered that various proteinases, proteinase-containing compositions, and particularly bromelain, can be effectively used to quickly reduce pain and inflammation at a site of a body that was previously exposed to capsaicin. Such discovery is particularly unexpected as capsaicin is clearly not a dipeptide (or any other type of protein), which is the natural substrate of bromelain. Formulae 1A-1C depict exemplary capsaicin compounds, which all include a peptide bond that is the presumed site of catalytic cleavage of contemplated proteinases.

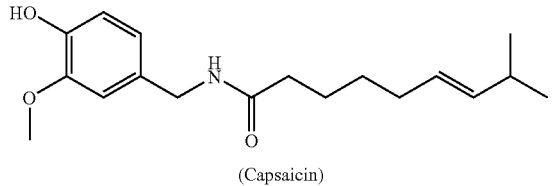

Formula 1A (Capsaicin)

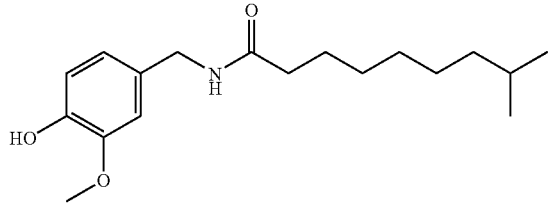

Formula 1B (Dihydrocapsaicin)

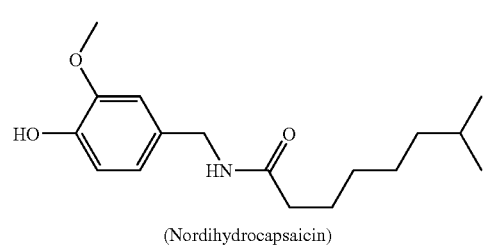

Formula 1C (Nordihydrocapsaicin)

Bromelain is a crude extract from the pineapple that contains, among other components, various closely related proteinases having diverse physiological effects. For example, bromelain was reported to reduce inflammatory responses in a person (see e.g., *Skin Therapy Lett.* 2000; 5(4):3-5, or *Integr. Cancer Ther.* 2002 March; 1(1):7-37). Further reported effects include in vitro and in vivo, antiedematous, antithrombotic, and fibrinolytic activities (see e.g., *Cell Mol Life Sci.* 2001 August; 58(9):1234-45). Remarkably, bromelain was also reported to reduce inflammation in combination with capsaicin as described in U.S. Pat. No. 5,560,910. However, the inflammation in those reported cases was due to an underlying disease condition (e.g., rheumatoid arthritis). However, the pain relieving effect of bromelain for treatment of capsaicin-induced pain was not recognized heretofore.

In one exemplary and preferred aspect of the inventive subject matter, an over-the-counter preparation of bromelain (e.g., Bromelain 2000 GDU/g [GDU: gelatin digesting units]; 200 mg capsules, commercially available from Iherb.com) is dissolved in water or fruit juice at a concentration of about 100 GDU/ml and topically applied to the capsaicin affected area using soft absorbent material (e.g., cotton cloth). If needed, the bromelain solution may also be dropped into an eye. In such applications, it is typically preferred that the treated body surface is rinsed after 1-10 minutes of the application to avoid proteolytic degradation of the treated tissue. Alternatively, or additionally, the bromelain solution may also be orally administered by swirling and/or gargling the solution in the oral cavity.

It should be recognized, however, that numerous bromelain concentrations other than 100 GDU/ml are also contemplated, and suitable concentrations may be in the range of 0.1 GDU/ml (and even less) to about 200 GDU/ml and higher. Viewed from another perspective, bromelain may be present in the solution at concentrations of 0.1 microgram/ml (and less where desired) up to 100 mg/l or even higher. Similarly, the solvent for the proteinase may vary considerably, and numerous alternative solvents are also deemed suitable. Generally, however, it is preferred that the solvent is an aqueous solvent, which may optionally include reducing agents (e.g., cysteine or glutathione), buffering agents (preferably to achieve a pH of about 8.0-8.5), flavoring agents, and/or preservatives. For example, suitable solvents include water, juice and other fruit-based or flavored drinks, and generally all nutritionally acceptable beverages. In less preferred aspects, the proteinase may also be in a dry form (e.g., as package with a single dose), and especially preferred dry forms include lyophilized, freeze dried, or otherwise dehydrated preparations of the proteinase. Such dry formulations may also include additional dry reagents to establish a preferred pH and/or provide reducing agent as discussed above. Where the proteinase is in dry form, it should be recognized that the amount of the proteinase may vary considerably. However, it is generally preferred that the amount is such that a single dose unit (e.g., tea spoon, single package content, etc.) will provide sufficient activity to reduce pain caused by exposure to capsaicin.

In still further contemplated aspects, the proteinase may also be formulated in a cream, ointment or other non-fluid topical preparation, which may be manually applied, and/or be applied under occlusion. There are numerous topical formulations known in the art, and all of such known formulations arte contemplated for use in conjunction with the teachings presented herein (see e.g. Cosmetic and Toiletry Formulations, Volume 8, by Ernest Flick; 2nd edition (Jan. 15, 2000); Noyes Publications; ISBN: 0815514549).

With respect to the bromelain, it should be appreciated that the bromelain preparation is preferably relatively concentrated (e.g., at least 500 GDU/g dry weight). However, in less preferred aspects of the inventive subject matter, plant preparations (typically from pineapple) may also be employed that include a proteinase at lower concentrations, so long as such lower concentrations are still effective in reducing capsaicin-induced pain. Additionally, it should also be appreciated that contemplated compositions may include one or more proteinases other than bromelain, and preferred alternative proteinases include various cysteine proteinases (e.g., papain, ficin), metalloproteinases, serine proteinases (e.g., trypsin, chymotrypsin), lysosomal, or bacterial proteinases. Where possible, it is preferred that the proteinase is derived from an edible source, and most preferably from a plant. However, recombinant proteinases are also deemed suitable herein. There are numerous proteinases and proteinase-containing compositions commercially available and known in the art, and all of such proteinase compositions are deemed suitable for use herein. Still further, it should be appreciated that the proteinase composition may include the proteinase at relatively high purity (e.g., at least 70 wt %), at moderate concentrations, (e.g., at least 40 wt %), or even at relatively low concentrations (e.g., 5-40 wt %, and even lower).

Similarly, it should be noted that preferred proteinase preparations are effective not only against capsaicin-induced pain, but also against pain induced by vanilloids and/or alkaloids other than capsaicin that induce a pain sensation and include an amide bond. For example, suitable capsaicin-like compounds include dihydrocapsaicin, nordihydrocapsaicin, homocapsaicin, and homodihydrocapsaicin.

Therefore, in another aspect of the inventive subject matter, it should be recognized that the nature of the proteinase is not limiting to the inventive subject matter presented herein, so long as the topically applied proteinase has at least one of an analgesic effect, an anti-inflammatory effect, and a capsaicin hydrolytic effect. Furthermore, contemplated compositions may also include analgesic and anti-inflammatory compounds, and particularly suitable additional agents include non-steroidal anti-inflammatory drugs and topical vasoconstrictive agents. Additional rinsing agents and/or detergents may be included to facilitate removal of residual capsaicin or enzymatic cleavage products.

In yet further aspects of the inventive subject matter, it is contemplated that the use of the proteinase-containing formulations need not be limited to alleviation of symptoms of accidental or intended exposure of capsaicin (typically via pepper spray), but may also be useful in situations where food is found to have an unacceptably high heat due to capsaicin. For example, a travel or restaurant kit may include a solution (or dried preparation) of contemplated proteinases that can be applied to or admixed with a food item to reduce the perceived heat of the food item. Included in such kit is preferably an instruction to use the solution (or dried preparation) to reduce the heat of a food item.

In a still further contemplated aspect of the inventive subject matter, the inventors also contemplate that the efficiency of a capsaicin-containing formulation may be preserved by adding a proteinase inhibitor to a capsaicin preparation. For example a pepper spray may include naturally occurring or synthetic proteinase inhibitors that reduce or even completely eliminate the effect that would otherwise be provided by a proteinase used by a person attempting to reduce the capsaicin effect. Suitable proteinase inhibitors are well known in the art, and especially preferred inhibitors include various cystatins and aprotinin. Alternatively, or additionally, contemplated compositions may also include oxidizing agents that inactivate a proteinase, which in many cases requires the presence of a reducing agent to be effective.

Similarly, it is contemplated that the efficiency of a capsaicin-containing formulation may be preserved by chemical modification of the capsaicin molecule in a manner such as to reduce susceptibility to or rate of hydrolysis by a proteinase. For example, the hydrogen atom in the NH group of the amide bond can be replaced by a non-hydrogen substituent (e.g., methyl, acyl, hydroxyl, etc.). Alternatively, or additionally, the oxygen in the amide group may be replaced by a sulfur to form the corresponding thioamide. Further contemplated modifications include modification of the substituents in the phenyl group of the capsaicin as well as modifications in the alkyl/alkenyl side chain of the capsaicin molecules.

Thus, specific embodiments and applications of personal protection, defense, and counter-defense compositions and methods have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. A method of relieving pain in a subject suffering from pain due to topical contact with capsaicin comprising:
    (a) Combining a proteinase with a formulation suitable for topical administration to yield a composition; and
    (b) Applying the composition of (a) topically to the site of pain;
    wherein the proteinase in the composition of (a) is in an amount effective to relieve the pain.

2. The method of claim 1 wherein the formulation is a liquid spray formulation.

3. The method of claim 1 wherein the proteinase is a cysteine proteinase or a serine proteinase.

4. The method of claim 1 wherein the proteinase is bromelain.

5. The method of claim 2 wherein the proteinase is present at a concentration of at least 10 GDU/ml.

6. The method of claim 1 wherein the formulation is suitable for administration into the eye.

7. The method of claim 1 wherein the formulation is a cream or ointment.

* * * * *